(12) United States Patent
Yomtov

(10) Patent No.: US 10,596,307 B2
(45) Date of Patent: *Mar. 24, 2020

(54) BLOOD PUMP FOR ISCHEMIA DETECTION AND TREATMENT

(71) Applicant: HeartWare, Inc., Miami Lakes, FL (US)

(72) Inventor: Barry M. Yomtov, Marblehead, MA (US)

(73) Assignee: HeartWare, Inc., Miami Lakes, FL (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/274,470

(22) Filed: Sep. 23, 2016

(65) Prior Publication Data

US 2017/0087289 A1 Mar. 30, 2017

Related U.S. Application Data

(60) Provisional application No. 62/232,601, filed on Sep. 25, 2015.

(51) Int. Cl.
*A61M 1/12* (2006.01)
*A61M 1/10* (2006.01)

(52) U.S. Cl.
CPC ............ *A61M 1/122* (2014.02); *A61M 1/101* (2013.01); *A61M 1/1005* (2014.02);
(Continued)

(58) Field of Classification Search
CPC ...... A61M 1/10; A61M 1/1005; A61M 1/101; A61M 1/1086; A61M 1/122;
(Continued)

(56) References Cited

U.S. PATENT DOCUMENTS

| 4,957,504 A | 9/1990 | Chardack |
| 5,290,227 A | 3/1994 | Pasque |

(Continued)

OTHER PUBLICATIONS

Choi et al., "Effect of counter-pulsation control of a pulsatile left ventricular assist device on working load variations of the native heart", BioMedical Engineering OnLine 2014, 13:35.

(Continued)

*Primary Examiner* — Eric D. Bertram
(74) *Attorney, Agent, or Firm* — Christopher & Weisberg, P.A.

(57) ABSTRACT

A blood pump incorporating a rotary pump such as a rotary impeller pump implantable in fluid communication with a ventricle and an artery to assist blood flow from the ventricle to the artery. The device may include a pump drive circuit supplying power to the pump, one or more sensors for sensing one or more electrophysiological signals such as subcutaneous, pre-cordial ECG signals and a signal processing circuit connected to the sensors and to the pump drive circuit. The signal processing circuit is operative to detect the sensor signals and control power supplied to the pump from the pump drive circuit so that the pump may run in a normal sinus rhythm mode, with a varying speed synchronized with the cardiac cycle. When an ischemic or myocardial infarction condition is detected, the pump drive circuit may also run the pump in an ischemia or myocardial infarction mode different from the normal sinus rhythm mode.

20 Claims, 6 Drawing Sheets

(52) U.S. Cl.
CPC ........ *A61M 1/1012* (2014.02); *A61M 1/1086* (2013.01); *A61M 2205/04* (2013.01); *A61M 2205/3303* (2013.01); *A61M 2205/3317* (2013.01); *A61M 2205/3365* (2013.01); *A61M 2230/04* (2013.01)

(58) Field of Classification Search
CPC ...... A61M 2205/33; A61M 2205/3303; A61M 2205/3365; A61M 2230/04
See application file for complete search history.

(56) References Cited

U.S. PATENT DOCUMENTS

| | | | |
|---|---|---|---|
| 5,383,840 | A | 1/1995 | Heilman et al. |
| 6,234,772 | B1 | 5/2001 | Wampler et al. |
| 6,264,635 | B1 | 7/2001 | Wampler et al. |
| 6,327,499 | B1 | 12/2001 | Alt |
| 6,669,624 | B2 | 12/2003 | Frazier |
| 6,949,066 | B2 | 9/2005 | Bearnson et al. |
| 6,969,345 | B2 | 11/2005 | Jassawalla et al. |
| 7,645,225 | B2 | 1/2010 | Medvedev et al. |
| 7,699,586 | B2 | 4/2010 | LaRose et al. |
| 2004/0172077 | A1 | 9/2004 | Chinchoy |
| 2005/0004476 | A1* | 1/2005 | Payvar .................... A61B 5/01 600/481 |
| 2005/0085683 | A1 | 4/2005 | Bolling et al. |
| 2007/0265703 | A1 | 11/2007 | Sutton et al. |
| 2008/0183287 | A1 | 7/2008 | Ayre |
| 2009/0112312 | A1 | 4/2009 | LaRose et al. |
| 2010/0076247 | A1* | 3/2010 | Zilbershlag ......... A61M 1/1031 600/17 |
| 2010/0114230 | A1 | 5/2010 | Audit |
| 2010/0204539 | A1 | 8/2010 | Tansley |
| 2011/0178361 | A1* | 7/2011 | Yomtov .................. A61M 1/10 600/16 |
| 2014/0343445 | A1 | 11/2014 | Scholz et al. |

OTHER PUBLICATIONS

International Patent Appl. No. PCT/US16/17148, entitled "Blood Pump for Treatment of Bradycardia," filed Feb. 9, 2016.
International Preliminary Report on Patentability issued by the International Bureau of WIPO dated Jul. 24, 2012 in connection with International Application No. PCT/US2011/021508.
Written Opinion of the International Searching Authority issued by the International Searching Authority (ISA/US) dated Apr. 15, 2011 in connection with International Application No. PCT/US2011/021508.
International Search Report issued by the International Searching Authority (ISA/US) dated Apr. 15, 2011 in connection with International Application No. PCT/US2011/021508.
International Search Report and Written Opinion for Application No. PCT/US16/17148 dated Apr. 29, 2016.
International Search Report and Written Opinion dated Dec. 21, 2016, for corresponding International Application No. PCT/US2016/053395; International Filing Date: Sep. 23, 2016 consisting of 9 pages.

* cited by examiner

BLOOD PUMP FOR ISCHEMIA DETECTION AND TREATMENT

CROSS-REFERENCE TO RELATED APPLICATIONS

This application claims the benefit of the filing date of U.S. Provisional Patent Application No. 62/232,601 filed Sep. 25, 2015, the disclosure of which is hereby incorporated herein by reference.

This application fully incorporates by reference U.S. Provisional Patent Application No. 62/119,895, entitled "Blood Pump for Treatment of Bradycardia."

FIELD OF THE INVENTION

The present invention relates to blood pumps and ventricular assist devices (VADs).

BACKGROUND OF THE INVENTION

Blood pumps are devices which are used to assist the heart of a mammalian subject such as a human patient. One type of blood pump known to those of skill in the art is a ventricular assist device ("VAD"). A VAD may include a pump which is implanted in the body of the subject (e.g., a human patient). The term "implanted" is given its art recognized meaning and the pumps described herein are sized and shaped in accordance with the requirements of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor that may be closely integrated with the pump. The motor in turn typically is powered by an implantable power source such as a storage battery with an arrangement for charging the battery from an external power source. The VAD may also include a control system which controls operation of the power source so as to drive the impeller at a set rotational speed and thus provide constant pumping action.

Blood pumps can be used to assist the heart of subjects suffering from conditions which impair the pumping ability of the heart. Such assistance can be provided permanently, or while the subject awaits a suitable heart implanted in accordance with its art recognized meaning, sized and shaped. In other cases, the assistance provided by the VAD allows the heart to heal.

BRIEF SUMMARY OF THE INVENTION

One aspect of the present technology provides a blood pump that may be implanted in the body, or located external to the subject. In a preferred embodiment, the blood pump is a ventricular assist device ("VAD"). While examples of the present technology are described herein as VADs, the present invention is not limited to VADs.

The blood pump desirably may include a rotary pump such as a rotary impeller pump that is implantable in a subject and in fluid communication with a ventricle and an artery of a patient to assist blood flow from the ventricle to the artery. The blood pump most preferably may further include at least one pump drive circuit and also preferably includes at least one sensor for sensing one or more electrophysiological signals such as subcutaneous ECG signals in the subject and providing sensor signals representing the electrophysiological signals.

The blood pump may also include a signal processing circuit connected to the sensors and the pump drive circuit. The signal processing circuit operates to receive the sensor signals, and control power supplied to the pump from the pump drive circuit(s) so that the pump runs in a normal sinus rhythm mode with a varying speed synchronized with the cardiac cycle of the subject. As disclosed herein, operation in the normal sinus rhythm mode provides improved assistance to the heart.

The signal processing circuit may also be operative to determine the presence or absence of a reduction in cardiac blood flow such as ischemia or angina, or total blockage of blood to the heart muscle as in myocardial infarction, based on the physiological sensor signals, and to control power supplied to the pump from the pump drive circuit so as to operate the pump in a normal sinus rhythm mode in the absence of a reduction in cardiac blood flow and to operate the pump in a modified mode of operation in the presence of a reduction in cardiac blood flow. For example, the modified mode may be a pulsatile mode with different operational parameters such as a higher speed as compared to the normal sinus rhythm mode. Or, the pump may operate in a non-pulsatile and at constant speed in the event of detecting a more severe ischemia or myocardial infarction.

DETAILED DESCRIPTION

Figure 1:
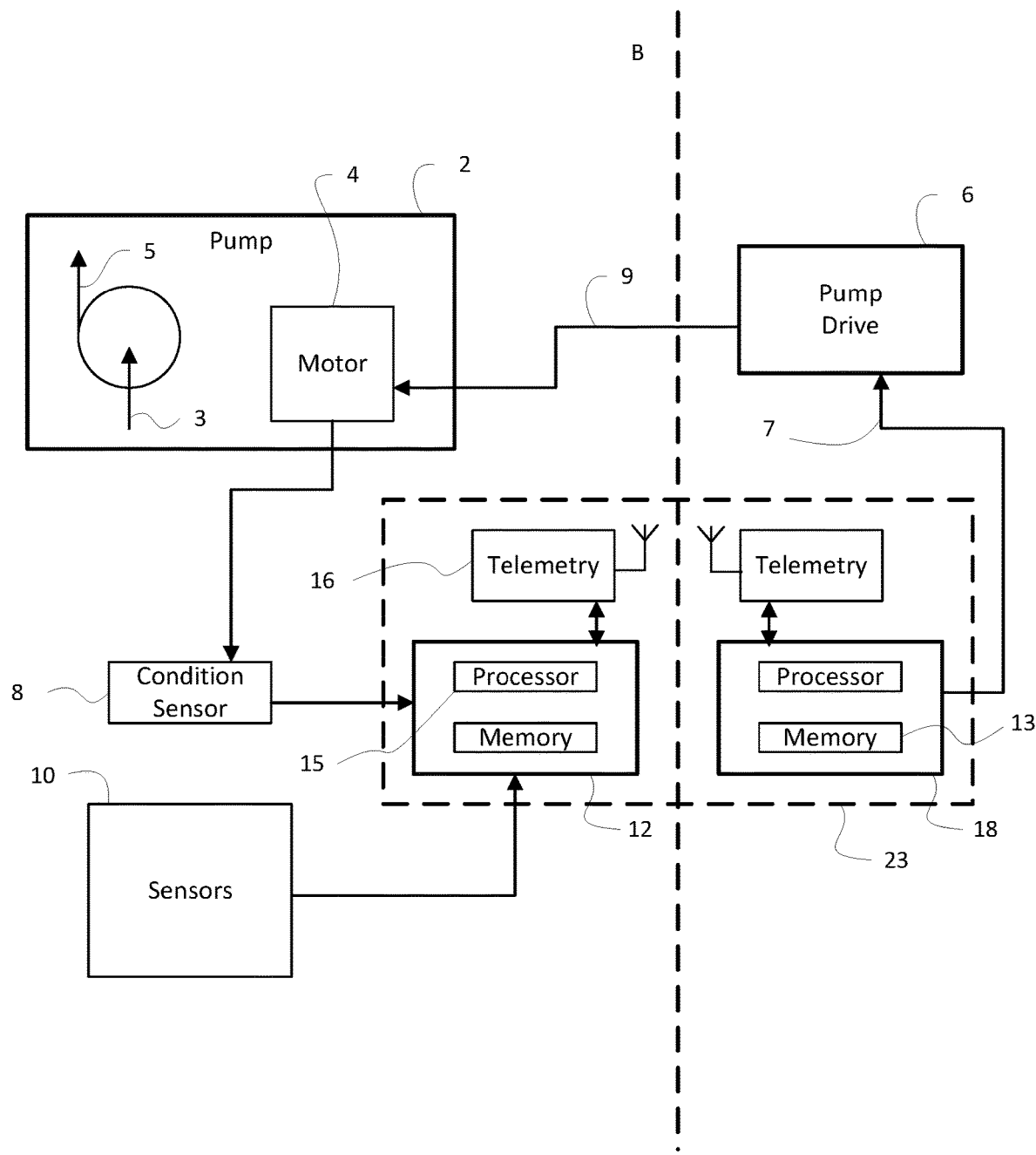
FIG. 1 is a functional block diagram of a blood pump in accordance with one embodiment of the invention.

In a preferred embodiment of the present invention, the blood pump is a VAD as shown in (FIG. 1). The VAD may include an implantable rotary pump 2, incorporating a motor 4. As used in this disclosure, the term "rotary pump" refers to a pump that incorporates a pumping element mounted for rotation in a housing. Most typically, the pump 2 is a rotary impeller pump having an impeller mounted within the housing, so that the spinning motion of the impeller transfers momentum to the fluid to be pumped. Although the pump 2 and motor 4 are depicted in FIG. 1 as separate components for clarity of illustration, in practice these components can be closely integrated with one another. For example, the impeller of the pump 2 may serve as the rotor of the motor 4. Most typically, the motor 4 is a multi-phase brushless direct current, permanent magnet motor arranged to drive the impeller of the pump 2 at a rotational speed prescribed by the motor driver by means of a motor commutation technique such as trapezoidal commutation. These components are sized and shaped so that the pump 2 can be implanted within the body of a mammalian subject, with the inlet 3 in fluid communication with a ventricle of the heart, most typically the left ventricle, and with the outlet 5 in fluid communication with an artery, most typically the aorta. For example, the pump 2 may be arranged for implantation outside of the heart, and the inlet and outlet may include conduits that can be surgically connected to the ventricle and the aorta.

In other arrangements, the pump 2 is arranged so that it may be implanted within the aorta and ventricle. Exemplary implantable pumps are described in detail in U.S. Pat. Nos. 6,264,635; 6,234,772; and 7,699,586; and U.S. Published Patent Application No. 20090112312. These patents and published patent applications, which are commonly assigned, are hereby incorporated by reference.

The VAD may also include at least one pump drive circuit 6. The pump drive circuit(s) 6 may include an electrical storage battery and a motor driver to control the motor. The output of the motor driver may be connected by an output connection, such as a cable 9 to the motor 4 of pump 2, so that the motor driver can drive the motor 4 and thus operate the pump 2. The motor driver may typically include semiconductor switching elements which are responsive to control signals applied at a control input 7, so that the current supplied to motor 4 can be controlled. In the particular arrangement depicted, pump drive circuit 6 may be mountable outside of the subject's body B and may be connected to the motor 4 by conductors which penetrate the skin of the subject. In other arrangements, the pump drive circuit 6 may be implanted within the subject's body and may be connected to an external power source by an inductive coupling or skin-penetrating conductors. The pump drive circuit may be used to apply power to the pump, control the speed of the pump, or both. Alternatively, two separate pump drive circuits may be used. In such an embodiment, a first pump drive circuit applies power to the pump and the second pump drive circuit controls the speed of the pump.

Pump 2 may be equipped with a condition sensor 8 such as a speed sensor. For example, the condition sensor may include a back EMF detector operative to detect voltage or current in the stator coils of motor 4 as a measure of motor speed or load.

The VAD may also include a signal processing circuit 23. The signal processing circuit 23 may include an implantable internal module 12 and an external module 18 arranged for mounting outside of the subject's body B. Modules 18 and 6 may also be implanted with the subject's body. The signal processing circuit 23 may be connected to the control input 7 of pump drive circuit 6. In this embodiment, modules 12 and 18 are connected to one another by a suitable signal transmitting arrangement such as radio frequency telemetry transmitting and receiving units 16 so that signals and data can be interchanged between the modules. Modules 12 and 18 may include conventional data processing elements such as one or more microprocessors 15 and one or more memory elements 13 arranged to perform the algorithms disclosed herein. The distribution of hardware elements and software functions between these modules can be varied over a wide range. In one embodiment, all of the data processing necessary to perform the algorithm is performed in external control module 18, and the internal module acts essentially as a conduit for data and signals. In another embodiment, all of the hardware and software required to perform the algorithms resides in the internal module 12, and the external module is omitted. The power required to operate the electronic circuitry of the internal module 12 typically is about 3 orders of magnitude less than the power required to drive motor 4.

The internal module 12 may be connected to receive power from the alternating current supplied by the pump drive circuit 6 to motor 4. This arrangement is particularly useful where the internal module 12 is physically located at the pump 2. Where the internal module of the signal processing circuit 23 is physically located at the pump 2, it may be desirable to provide magnetic shielding between the coils of the pump motor 4 and the circuitry of the internal module 12. Alternatively, where the internal module 12 is located away from the pump 2, then the signal processing circuitry 23 can receive power from an internal battery such as a primary battery or rechargeable battery.

Figure 5:
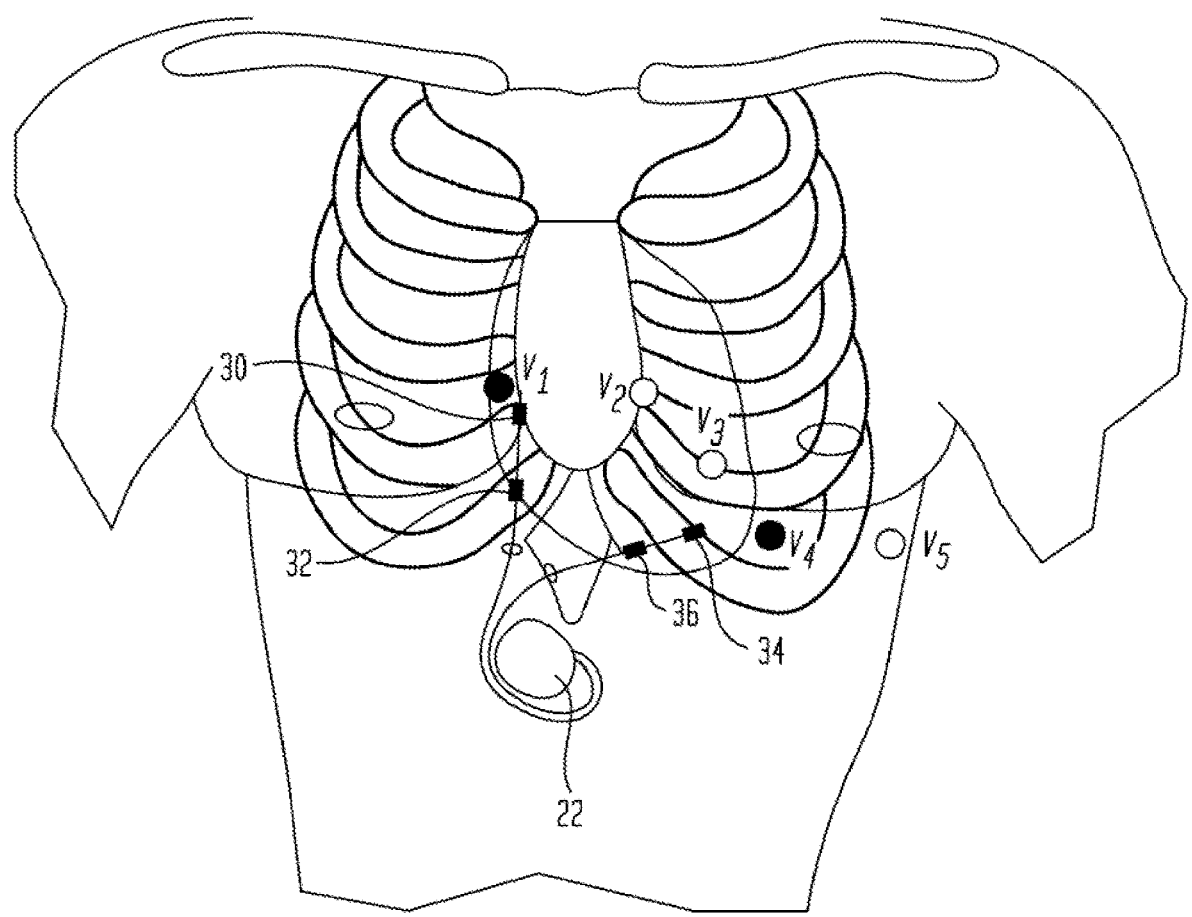
FIG. 5 is a diagram depicting the lead and electrode implantation for the cardiac monitoring of reduced cardiac blood flow

The VAD further includes sensors 10 which may be connected to the internal module 12 of the signal processing circuit 23. As shown in greater detail in FIG. 5, the sensors include subcutaneous electrodes implanted at pre-cordial (or chest) locations similar to a 12-lead ECG cardiac monitor such as designations V1 through V6. Recordings from these electrodes could be of unipolar configuration with a far field remote anode 41, such as the conductive titanium case of the implanted electronics 22 connected to receive electrical signals from the subcutaneous pre-cordial electrodes 30, 32, 34, 36. The electrical recordings could also be bipolar with respect to pairs of electrodes. When the VAD is implanted, the subcutaneous pre-cordial electrodes 30, 32, 34, and 36 are disposed at appropriate locations near the heart of the subject.

The sensors 10 also may include one or more physiological condition sensors 43. The physiological condition sensors 43 may be used to sense and transmit any type of physiological parameter, such as oxygen concentration, pressure within a vessel or chamber, and temperature. Sensors 10 may also include one or more further sensors 45 arranged to provide a signal representing a parameter related to cardiac demand. For example, the further sensors 45 may include one or more accelerometers arranged to provide signals representing movement of the patient's body B. There may be a positive correlation between the amount of movement and cardiac demand.

The various sensors are connected to the internal module 12 of the signal processing circuit 23 through appropriate signal conditioning elements such as an analog to digital converter 47 and buffer memory 49.

Signal processing circuit 23 may be configured with functionality to receive, analyze and process signals received from sensors as they relate to the physiological condition of the patient. Some of this functionality may include processing signals from sensors 10 to determine the phase of the patient's cardiac cycle, sensing the patient's intrinsic heart rate; determining the patient's metabolic demand, and detecting a reduction of blood flow to the heart during conditions of ischemia or during more significant reduction as with myocardial infarction, and in response to those signals, may set the mode of operation and speed of the pump 2 accordingly. The signal processing circuit 23 may also control the frequency of the motor drive signal to the pump 2.

Figure 3:
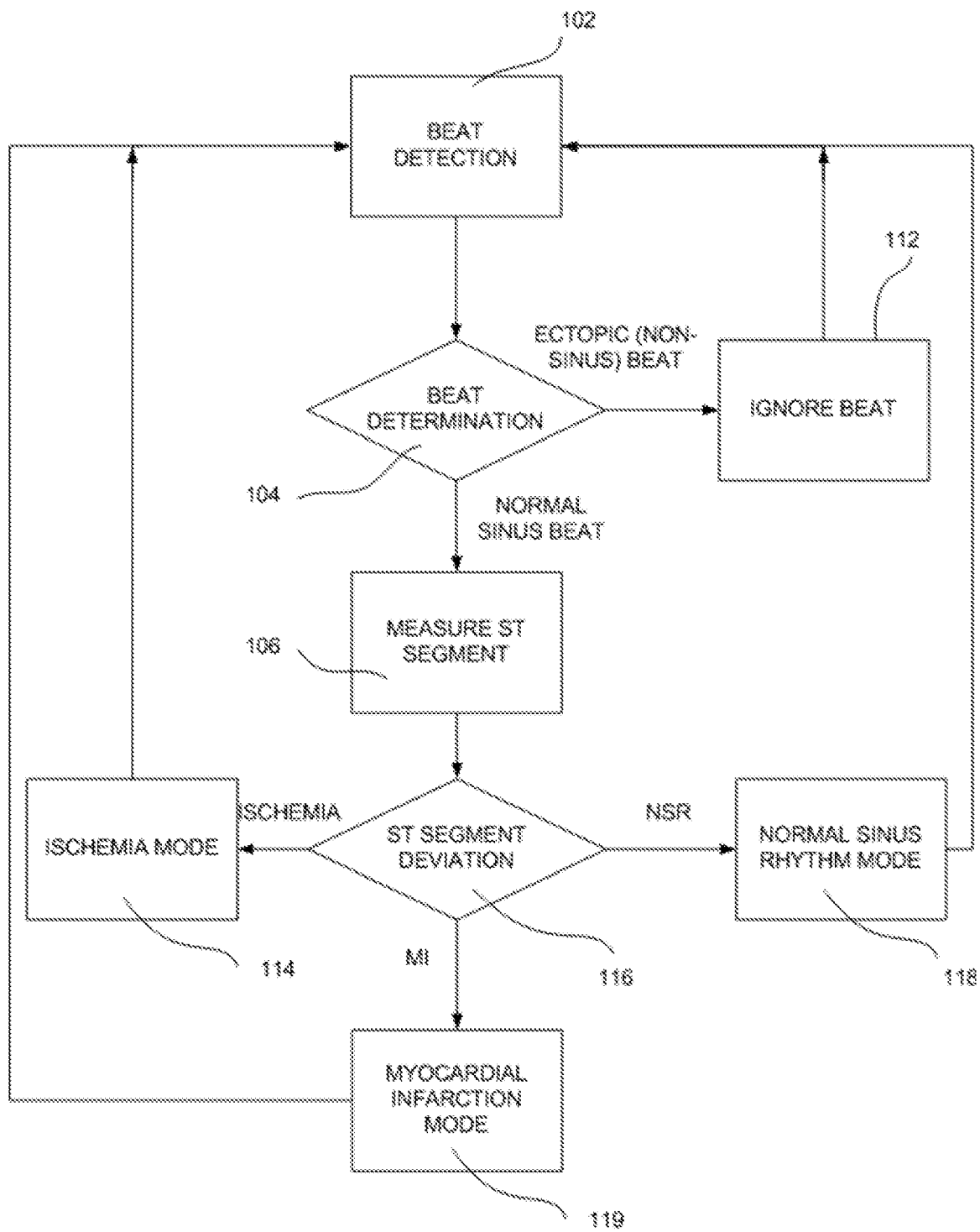
FIG. 3 is a flowchart depicting a portion of an algorithm used in operation of the blood pump of FIGS. 1 and 2.

Signal processing circuit 23 may be specifically configured to repeatedly execute an algorithm as shown in simplified form in FIG. 3. At step 102, a processor 15 may execute a beat detection routine using signals acquired from the subcutaneous electrodes 30, 32, 34 and 36. Beat detection algorithms based on pre-cordial electrode signals are known in the art and are commonly employed in devices such as 12 lead ECG cardiac monitors. Any detection circuit or algorithm routine which is effective to discriminate a normal sinus beat versus an ectopic (non-sinus) beat can be employed.

At step 104, the algorithm branches depending on the results of the individual beat detection. If the detection has determined by processor 15 that the subject's heart is a non-sinus (or an ectopic beat), the algorithm ignores the beat 112 and returns to the beat detection algorithm 102. If the beat determination algorithm 104 as determined by the processor 15 that the beat is of normal sinus origin, then the algorithm moves on to the ST segment measurement function 106 which would be performed by processor 15. Once the ST segment amplitude is measured 106 by the processor 15, the algorithm determines whether there is a ST segment level deviation sufficiently greater than a specified amplitude (positive and/or negative) 116. This ST segment measurement by processor 15 may also be determined by calculating a moving average of multiple detected normal sinus beats. The moving average data may be stored in memory 13. If the ST segment measurement exceeds a specified threshold for an ischemic condition, then the algorithm determines that an ischemic reduction of blood flow to the cardiac muscle has occurred, the VAD pump drive 6 is instructed to operate in an ischemia mode 114 as prescribed (e.g., programmed) by the physician and controlled by processor module 18. For example the ischemia operational conditions may be an increase in the pulsatile speed while still synchronized to the natural heart beat. Depending upon the magnitude and polarity of the ST segment deviation, the algorithm may determine that the cardiac muscle is in a myocardial infarction condition. If the ST segment measurement exceeds a threshold indicative of a myocardial infarction, the VAD pump drive 6 is instructed by the processor module 18 to operate in an myocardial infarction mode 119 as prescribed (e.g., programmed) by the physician. For this condition, the myocardial infarction mode may be to switch the pump drive 6 to a constant speed mode in order to increase the cardiac output.

Figure 4A:
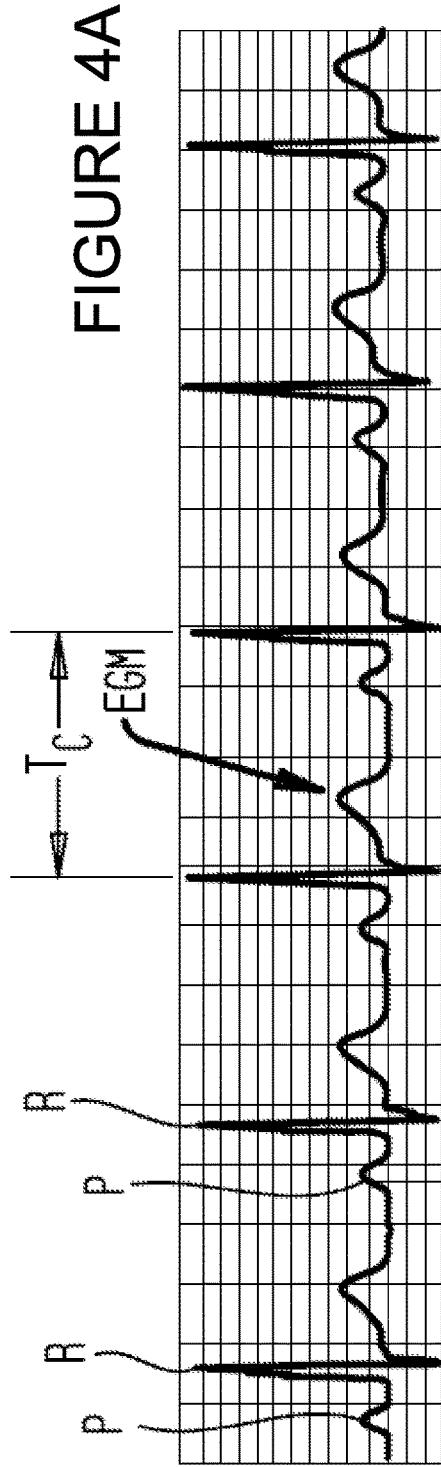
FIGS. 4A and 4B are graphs of certain signals and variables occurring in operation of the blood pump of FIGS. 1-3.
Figure 4B:
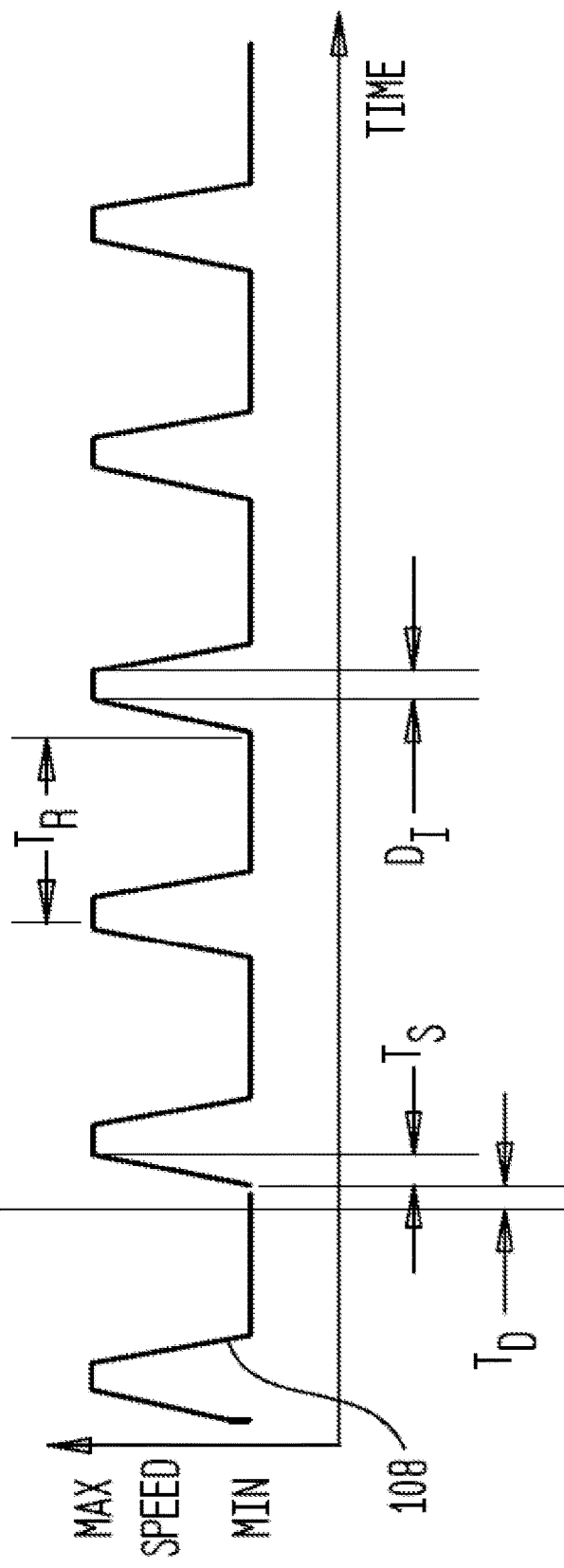

If there is no ischemia or myocardial infarction detected, then the VAD may continue to operate in the normal sinus rhythm mode 118. In this mode, the signal processing circuit 23 actuates pump drive circuit 6 to vary the speed of the pump 2 between a minimum speed and a maximum speed, as depicted by curve 208 (FIG. 4B). The pattern of variation in the speed of the pump 2 is synchronized with the intrinsic rhythm of the patient's heart as shown by the subcutaneous ECG signals so that the variation in speed of the pump 2 has a substantially fixed phase relationship to the intrinsic rhythm of the heart. Most preferably, the pump 2 operates at maximum speed during ventricular systole, when the ventricles contract to expel blood. The ECG curve shown in FIG. 4A is a schematic depiction showing a conventional external electrocardiogram waveform, which represents a composite of the electrical signals in the entire heart. In practice, the actual subcutaneous ECG signals appearing on electrodes 30, 32, 34, and 36 (FIG. 5) would be recorded and/or measured as separate signals. The recorded data may be stored in memory 13 for future analysis against suspected non-sinus beats.

Figure 6:
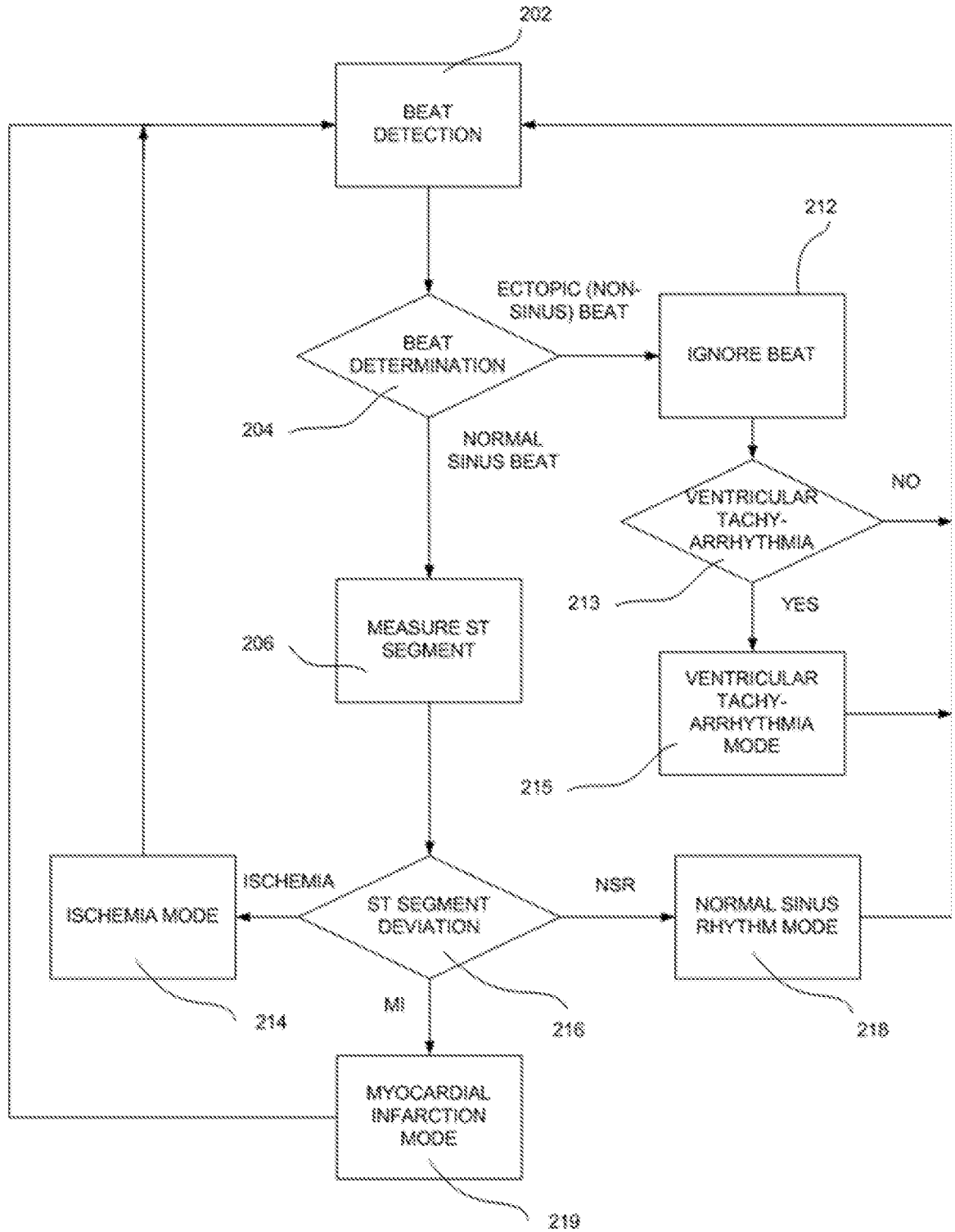
FIG. 6 is a flowchart of another embodiment depicting a portion of an algorithm used in operation of the VAD of FIGS. 1 and 2.

In another embodiment, signal processing circuit 23 repeatedly executes an algorithm as shown in simplified form in FIG. 6. At step 202, a processor may execute a beat detection routine using signals acquired from the subcutaneous electrodes 30, 32, 34 and 36. Beat detection based on pre-cordial electrode signals are well known in the art and are commonly employed in devices such as 12 lead ECG cardiac monitors. Any detection circuit or algorithm routine which is effective to detect a normal sinus beat versus an ectopic (non-sinus) beat can be programmed into the processor 15.

At step 204, the algorithm branches depending on the results of the individual beat detection. If the detection has determined that the subject's heart is a non-sinus beat, the algorithm ignores the beat 212 and continues with the ventricular tachy-arrhythmia rhythm detection algorithm 213. If the ventricular tachy-arrhythmia rhythm detection algorithm determines that there is no ventricular tachy-arrhythmia rhythm present, and is a non-sustained condition, then the algorithm returns to the beat detection 202. If the ventricular tachy-arrhythmia detection 213 determines that a ventricular tachy-arrhythmia is present, the algorithm enters a ventricular tachy-arrhythmia mode 215.

If the beat detection algorithm 204 determines that the beat is of normal sinus origin, then the algorithm moves on to the ST segment measurement function 206. Once the ST segment amplitude is measured, the algorithm determines whether there is a ST segment level deviation 216 sufficiently greater than a specified amplitude (positive and/or negative) as calculated by the processor 15. This ST segment measurement may also be determined by calculating a moving average of multiple detected normal sinus beats. The moving average data may be stored in memory 13.

If the ST segment measurement exceeds a specified threshold for an ischemic condition, then the algorithm determines that an ischemic reduction of blood flow to the cardiac muscle has occurred, the VAD is instructed to operate in an ischemia mode 214 as prescribed (e.g., programmed) by the physician and controlled by processor module 18. Depending upon the magnitude and polarity of the ST segment deviation, the algorithm may determine that the cardiac muscle is in a myocardial infarction condition.

If the ST segment measurement exceeds a threshold indicative of a myocardial infarction, the VAD pump drive 6 is instructed by the processor module 18 to operate in an myocardial infarction mode 219 as prescribed (e.g., programmed) by the physician. For this condition the myocardial infarction mode may be to switch the pump drive 6 to a constant speed mode in order to increase the cardiac output.

If there is no reduction in cardiac blood flow detected, then the VAD operates in the normal sinus rhythm mode 218. In this mode, the signal processing circuit 23 actuates pump drive circuit 6 to vary the speed of the pump 2 between a minimum speed and a maximum speed, as depicted by curve 208 (FIG. 4B).

The pattern of variation in the speed of the pump 2 is synchronized with the intrinsic rhythm of the patient's heart as shown by the subcutaneous ECG signals so that the variation in speed of the pump 2 has a substantially fixed phase relationship to the intrinsic rhythm of the heart. Most preferably, the pump 2 operates at maximum speed during ventricular systole, when the ventricles contract to expel blood.

The ECG curve shown in FIG. 4A is a schematic depiction showing a conventional external electrocardiogram waveform, which represents a composite of the electrical signals in the entire heart. In practice, the actual subcutaneous ECG signals appearing on electrodes 30, 32, 34, and 36 (FIG. 5) may be separate signals. Each electrode may provide additional electrical vectors (view) of the cardiac contraction as indicated during the QRS of the heart beat.

As ventricular systole occurs during the R-wave of the subcutaneous ECG representing ventricular depolarization, the pump 2 desirably reaches maximum speed at a time close to the timing of the R-wave. The signal processing circuit 23 can use various features of the subcutaneous ECG signals as the basis for synchronization. An ECG signal of the left ventricle using subcutaneous electrodes 34 or 36 (FIG. 5) provides the timing of the ventricular depolarization. The signal processing circuit 23 can simply actuate pump drive circuit 6 to increase the speed of pump 2, each time the left ventricle signal indicates beginning of ventricular depolarization, e.g., at the beginning of the R-wave. However, the mechanical components of pump 2 have inertia and require a finite time to accelerate from minimum speed to maximum speed. This time is referred to herein as the slew time $T_S$ (FIG. 4B). To allow for this effect, the signal processing circuit 23 may actuate the pump drive circuit 6 to progressively increase speed of the pump 2 over a period equal to $T_S$.

The signal processing circuit 23 can time the beginning of this period $T_R$ from the R-wave of the preceding cardiac cycle. The cycle time $T_C$ of the cardiac cycle is simply the inverse of the heart rate. Thus, the signal processing circuit 23 can initiate the increase in the pump speed at a time $T_R$ after the R-wave of the preceding cycle, where $T_R=T_C-T_S$. Provided that the heart rate is constant or varying slowly, and that the signal processing circuit 23 updates the heart rate and recalculates $T_C$ frequently, this simple arrangement can yield reasonable synchronization of the pump speed increase with the onset of ventricular systole. The cycle time $T_C$ used in this calculation can be based on a moving average of the cycle time over a few cycles.

Alternatively or additionally, the signal processing circuit 23 can measure the synchronization achieved during each cardiac cycle and advance or retard the initiation of pump acceleration. For example, if $T_R$ was too short in the preceding cycle, so that the pump 2 reached full speed before the R-wave, the signal processing circuit 23 can increase $T_R$ for the next cycle. Thus, the signal processing circuit 23 can act as a phase-locked loop holding the pump speed waveform in synchronization with the intrinsic cardiac cycle of the patient. In this arrangement, the cyclic variation of pump speed has a fixed phase relationship to the R-wave. In a variation of this arrangement, the measurement of synchronization can be a moving average representing the last few cardiac cycles.

In normal sinus rhythm, there is a substantially constant interval from the P-wave to the R-wave in each cardiac cycle. This interval can be estimated from the heart rate or can be determined directly from measurement of the subcutaneous ECG signals. Thus, the signal processing circuit 23 can time a period $T_D$ (FIG. 4B) after each P-wave and initiate pump acceleration at the end of this period. $T_D$ may be selected to equal the P-wave to R-wave interval minus $T_S$. In some instances, $T_S$ may be equal to the P-wave to R-wave interval, in which case $T_D$ may be zero. In this arrangement, the cyclic variation of pump speed has a fixed phase relationship to the P-wave.

Many other features of the subcutaneous ECG can be used as the basis for synchronization. Software routines for recognizing individual features of the waveforms such as the P-wave, and QRS complex of an ECG are known per se and any such routine can be used in the synchronization scheme.

Synchronizing the VAD with the patient's intrinsic depolarization will allow the pump 2 to operate when it is most advantageous to do so. Cardiac output is greatest during contraction of the atria and ventricles. In a weak or diseased heart, contraction of the chambers, and particularly the left ventricle is when assistance from a VAD is most critical. Therefore timing of the pump 2 with ventricular contraction will provide the optimal assistance to the patient and maximize the therapeutic effect of the VAD. Moreover, operation in a pulsatile mode synchronized to the subject's cardiac cycle can improve efficiency and thus conserve power.

While the synchronization of the pump 2 can be triggered by the actual occurrence of an electrophysiological signal, it is also possible to program the signal processing circuit 23 to anticipate the impending occurrence of a particular subcutaneous ECG waveform. For example, it is well known that each phase of the cardiac cycle should last for approximately the same duration of time in healthy patients. Through a programmed algorithm, the processor could be programmed by methods known in the art to measure and store historical patient data in a memory 13. This memory 13 could be located anywhere within the circuitry of the VAD, or externally.

The data would include of how long each phase of the cardiac cycle lasts in a given patient in a predetermined time. Measurements taken and stored over time can be used to determine through any mathematic or statistical means known, when the next phase of the cardiac cycle should begin in a given patient. This method would allow the processor 15 to instruct the pump drive circuit 6 when to accelerate the pump 2, based on an anticipated subcutaneous ECG waveform. Because atrial and ventricular systole is signaled by the beginning of the P-wave and R-wave respectively, the historical analysis of these phases of the cardiac cycle could be used to predict the onset of systole.

This predictive method of synchronizing the pump 2 with an actual or anticipated subcutaneous ECG waveform is of particular use in patients suffering from left side heart failure. Left side heart failure is a challenging pathology predominantly affecting the left ventricle. Patients with left side failure require assistance in order to maximize the efficiency of the left ventricular contraction. In one embodiment of the present invention, the signal processing circuit 23 will receive subcutaneous ECG waveform signal information from a patient with left sided heart failure. The signal processing circuit 23 will analyze the signal information and determine when an R-wave is occurring or is about to occur. Upon detecting the occurrence or impending occurrence of the complex, the signal processing circuit 23 will instruct the motor 4, through the pump drive circuit 6, to operate in order to drive the pump 2 in synchronism with the patient's own ventricular systole.

The signal processing circuit 23 can set the duration $D_I$ (FIG. 4B) of pump operation at maximum speed during each cardiac cycle based on the historical timing of the patient's R-waves. Alternatively, $D_I$ can be set as a fixed proportion of the cardiac cycle time $T_C$. In yet another variant, the signal processing circuit 23 is arranged so that $D_I$, or the routine used to set $D_I$, can be selected by the physician. Typically, $D_I$ is selected so that the pump 2 operates at maximum speed during most or all of ventricular systole.

Figure 2:
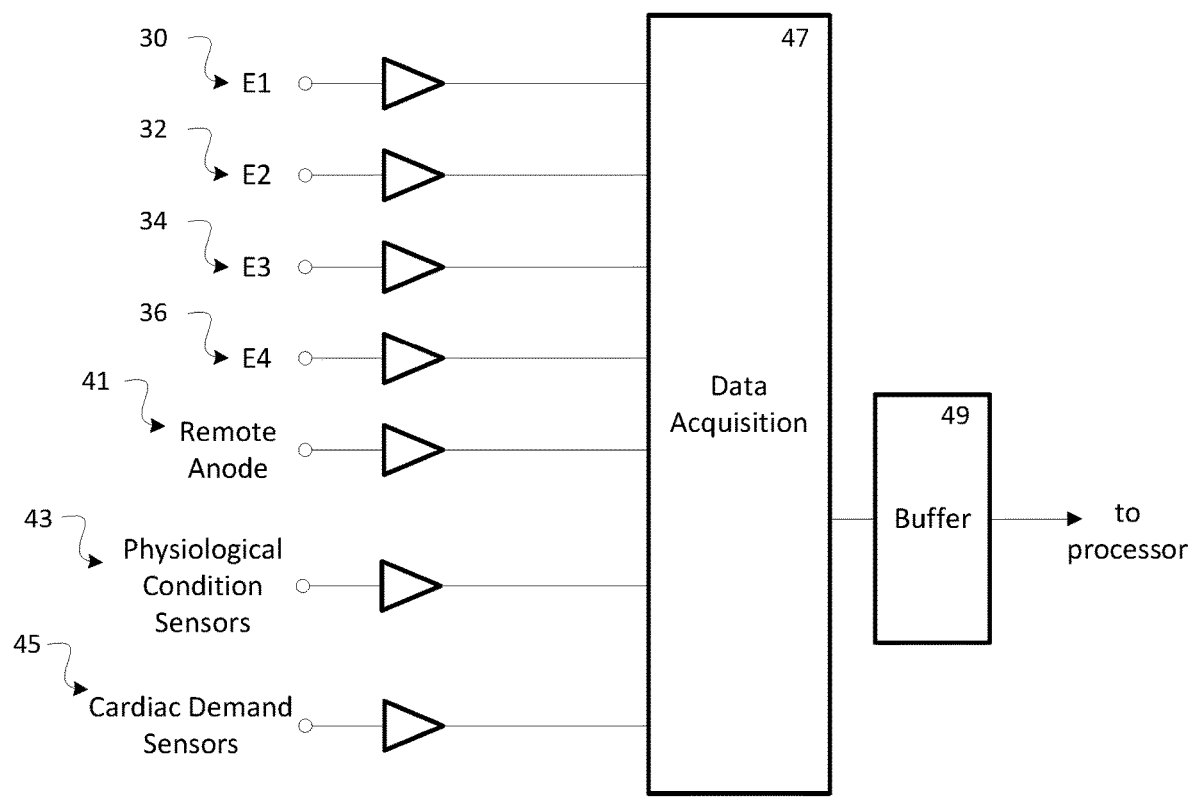
FIG. 2 is a schematic diagram depicting a portion of the blood pump of FIG. 1.

The maximum speed of the pump 2 or the $D_I$ can be a fixed value, or can be set by the signal processing circuit 23 depending on sensed data indicating the current status of the patient. For example, the maximum speed may increase with the heart rate as determined by the subcutaneous ECG signals from the electrodes, or as determined based on readings from physiological condition sensor 43 (FIG. 2), cardiac demand parameter sensor 45 or some combination thereof. Thus, the maximum speed may vary depending on whether the patient is sleeping, awake, and/or exercising. The minimum speed typically is non-zero speed, so that the pump 2 runs continually but speeds up and slows down during each cycle. For example, some rotary impeller pumps utilize hydrodynamic bearings to maintain a pump rotor out of contact with a surrounding pump housing, so that the pump operates with zero wear on the rotor and housing. These hydrodynamic bearings become ineffective when the rotor speed falls below a minimum pump operating speed. When the pump 2 incorporates such bearings, the minimum speed set by the signal processing circuit 23 desirably is set at or above the minimum pump operating speed. The minimum speed can also vary depending on sensed data.

Curve 208 (FIG. 4B) depicts one example of the speed variation as a progressive ramp-up from minimum to maximum, followed by operation at maximum, followed by ramp-down to minimum and operation at minimum. However, the pattern of speed variation can be more complex, with the speed continuously varying during the entire cycle. Here again, however, the pattern of speed variation is synchronized with the patient's intrinsic cardiac cycle in the manner described above.

The VAD continues to operate in the normal sinus rhythm mode described above while the signal processing circuit 23 continuously executes beat detection 102 (FIG. 3). So long as the patient remains in normal sinus rhythm, the normal sinus rhythm mode 118 operation continues. However, if an ischemia condition is detected, the program passes to step 114, where the signal processing circuit 23 actuates pump drive circuit 6 to operate the pump 2 in a mode referred to herein as the ischemia mode 112. In one arrangement, the ischemia mode 114 is a constant-speed mode in which the pump 2 runs at a constant speed and the pump speed does not vary during the cardiac cycle. In ischemia, constant speed mode, signal processing circuit 23 actuates the pump drive circuit 6 to supply power at a constant frequency to the motor 4 of pump 2, so that the pump 2 operates at a constant speed. This speed desirably is less than the maximum speed used during pulsatile operation. While the pump speed is substantially constant during the cardiac cycle, the signal processing circuit 23 can alter the constant speed depending on conditions detected by the physiologic sensor 43.

In another arrangement, the ischemia mode 114 or the myocardial infarction mode 119 may be a pulsatile mode in which variation of the pump speed is synchronized to the sinus beats. The signal processing circuit 23 may be programmed to include an algorithm to select either a pulsed mode (synchronous or asynchronous) or constant speed mode in response to detecting an ischemia condition or myocardial infarction condition and depending on conditions such as metabolic demand.

While the VAD is in ischemia mode 114, the signal processing circuit 23 continually executes the beat detection routine 102 and the ST segment measurement routine 106. If routine 106 detects a return to normal sinus rhythm, indicating that the ischemia condition has passed, the normal sinus rhythm mode 118 is restored as the pump drive 6 is instructed by the processor module 18. With a long term implant like a VAD, the normal sinus rhythm subcutaneous ECG data would be stored in memory 15 and may be updated on a continuous basis to reflect subtle changes to the baseline waveform and rhythm. This ongoing update of the normal sinus rhythm waveform would be performed by processor 13 and the updated waveforms stored in memory 15.

In still other embodiments, the ischemia detection and myocardial infarction detection, and the response discussed above can be applied in VADs having pumps other than rotary pumps.

While various elements have been described above as individual components depicted in functional block diagrams, these elements can be combined with one another. Conversely, elements shown as unitary elements in the functional block diagrams discussed above can be separated into separate elements. Also, the features described above with reference to different embodiments of the invention can be combined with one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A blood pump, comprising:
   a rotary pump configured to be implantable in a subject and in fluid communication with a ventricle and an artery of the subject to assist blood flow from the ventricle to the artery;
   at least one pump drive circuit for applying power to the pump, controlling the speed of the pump or both;
   at least one sensor for sensing one or more electrogram (ECG) signals in the subject; and
   a signal processing circuit in communication with the sensors and the at least one pump drive circuit, the signal processing circuit being operative to:
   (i) receive subcutaneous ECG signals,
   (ii) determine the presence of cardiac ischemia or a myocardial infarction condition based on subcutaneous pre-cordial electrode signals, and
   (iii) control the power supplied to the pump from the at least one pump drive circuit so as to control the speed of the pump and operate the pump in a normal sinus rhythm mode in the absence of an ischemic condition or myocardial infarction condition,
   (iv) to operate the pump in at least one modified mode of operation based on the presence of an ischemic condition or myocardial infarction condition, the at least one modified mode of operation includes at least one ischemia mode different from the normal sinus rhythm mode, the at least one ischemia mode includes a pulsatile mode different from the normal sinus rhythm mode.

2. The blood pump of claim 1, wherein the pump is a rotary impeller pump.

3. The blood pump of claim 1, wherein the signal processing circuit is operative to adjust the pump speed responsive to a condition of the subject.

4. The blood pump of claim 3, wherein the signal processing circuit adjusts the varying speed in accordance with electrophysiological signals that it receives from the at least one sensor.

5. The blood pump of claim 4, wherein the electrophysiological signals include subcutaneous ECG waveforms.

6. The blood pump of claim 5, wherein the subcutaneous ECG waveforms include at least one unipolar signal.

7. The blood pump of claim 5, wherein the subcutaneous ECG waveforms include at least one bipolar signal from a pair of electrodes.

8. The blood pump of claim 1, in which the signal processing circuit is operative to control power supplied to the pump so that the varying speed has a substantially fixed phase relationship with the P-wave of the subject's cardiac cycle.

9. The blood pump of claim 1, in which the signal processing circuit is operative to control power supplied to the pump so that the varying speed has a substantially fixed phase relationship with the R-wave of the subject's cardiac cycle.

10. The blood pump of claim 9, wherein the substantially fixed phase relationship of the varying speed with the R-wave of the subject's cardiac cycle is relative to a moving average cycle time over a number of cardiac cycles.

11. The blood pump of claim 1, wherein the at least one ischemia mode includes a non-pulsatile mode such that the pump runs in a non-pulsatile manner.

12. The blood pump of claim 1, wherein the at least one pulsatile mode includes an increase in pump speed for increased cardiac output.

13. The blood pump of claim 1, wherein the at least one ischemia mode includes a pulsatile mode wherein the pump runs in a pulsatile manner unsynchronized with the cardiac cycle of the subject.

14. The blood pump of claim 1, wherein the circuit is operable to detect a myocardial infarction condition and the at least one modified mode of operation includes at least one myocardial infarction mode different from the normal sinus rhythm mode.

15. The blood pump of claim 14, wherein the at least one myocardial infarction mode includes a non-pulsatile mode wherein the pump runs in a non-pulsatile manner.

16. The blood pump of claim 14, wherein the at least one myocardial infarction mode includes a pulsatile mode different from the normal sinus rhythm mode.

17. The blood pump of claim 14, wherein the at least one myocardial infarction mode includes a pulsatile mode wherein the pump runs in a pulsatile mode unsynchronized with a cardiac cycle of the subject.

18. The blood pump of claim 17, wherein the at least one pulsatile mode includes an increase in pump speed for increased cardiac output.

19. The blood pump of claim 1, wherein the at least one modified mode includes a non-pulsatile mode and wherein the signal processing circuit is operative via the motor drive to control power supplied to the pump so as to vary the speed of the pump in the non-pulsatile mode based on a condition of the subject.

20. The blood pump of claim 1, wherein at least one modified mode includes a ventricular tachy-arrhythmia mode in response to a detected tachy-arrhythmia condition.

* * * * *